(12) United States Patent
Chen et al.

(10) Patent No.: US 11,730,811 B2
(45) Date of Patent: Aug. 22, 2023

(54) METHOD FOR TREATING SUBJECT SUFFERING FROM FLAVIVIRUS INFECTION

(71) Applicant: Kaohsiung Medical University, Kaohsiung (TW)

(72) Inventors: Yen-Hsu Chen, Kaohsiung (TW); Chun-Yu Lin, Kaohsiung (TW); Paraskevi Heldin, Uppsala (SE)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 0 days.

(21) Appl. No.: 17/203,978

(22) Filed: Mar. 17, 2021

(65) Prior Publication Data

US 2021/0205450 A1    Jul. 8, 2021

Related U.S. Application Data

(63) Continuation-in-part of application No. 15/881,350, filed on Jan. 26, 2018, now abandoned.

(30) Foreign Application Priority Data

Oct. 5, 2017  (TW) ................................. 106134411

(51) Int. Cl.
| | | |
|---|---|---|
| *A61K 39/42* | (2006.01) |
| *A61K 39/395* | (2006.01) |
| *C07K 16/28* | (2006.01) |
| *C12N 15/113* | (2010.01) |
| *A61K 31/37* | (2006.01) |
| *A61P 31/14* | (2006.01) |
| *A61K 38/47* | (2006.01) |
| *A61K 39/00* | (2006.01) |

(52) U.S. Cl.
CPC .......... *A61K 39/3955* (2013.01); *A61K 31/37* (2013.01); *A61K 38/47* (2013.01); *A61P 31/14* (2018.01); *C07K 16/2884* (2013.01); *C12N 15/1138* (2013.01); *A61K 2039/505* (2013.01); *A61K 2039/545* (2013.01); *C12N 2310/14* (2013.01)

(58) Field of Classification Search
None
See application file for complete search history.

(56) References Cited

U.S. PATENT DOCUMENTS

2010/0267714 A1* 10/2010 Jorgensen ............ C07D 401/06
548/255

FOREIGN PATENT DOCUMENTS

| CN | 104561000 A | * | 4/2015 | |
|---|---|---|---|---|
| JP | 10-082784 A | | 3/1998 | |
| WO | WO-02072803 A2 | * | 9/2002 | ............. A61K 39/12 |

(Continued)

OTHER PUBLICATIONS

EPO English translation of CN 104561000A (Year: 2015).*

(Continued)

*Primary Examiner* — M Franco G Salvoza
(74) *Attorney, Agent, or Firm* — Volpe Koenig

(57) ABSTRACT

The present invention discloses a method for treating a subject suffering from a Flavivirus infection. The method includes a step of administering to the subject a pharmaceutical composition including a pharmaceutically effective amount of an anti-CD44 antibody.

11 Claims, 7 Drawing Sheets

Figure 1:
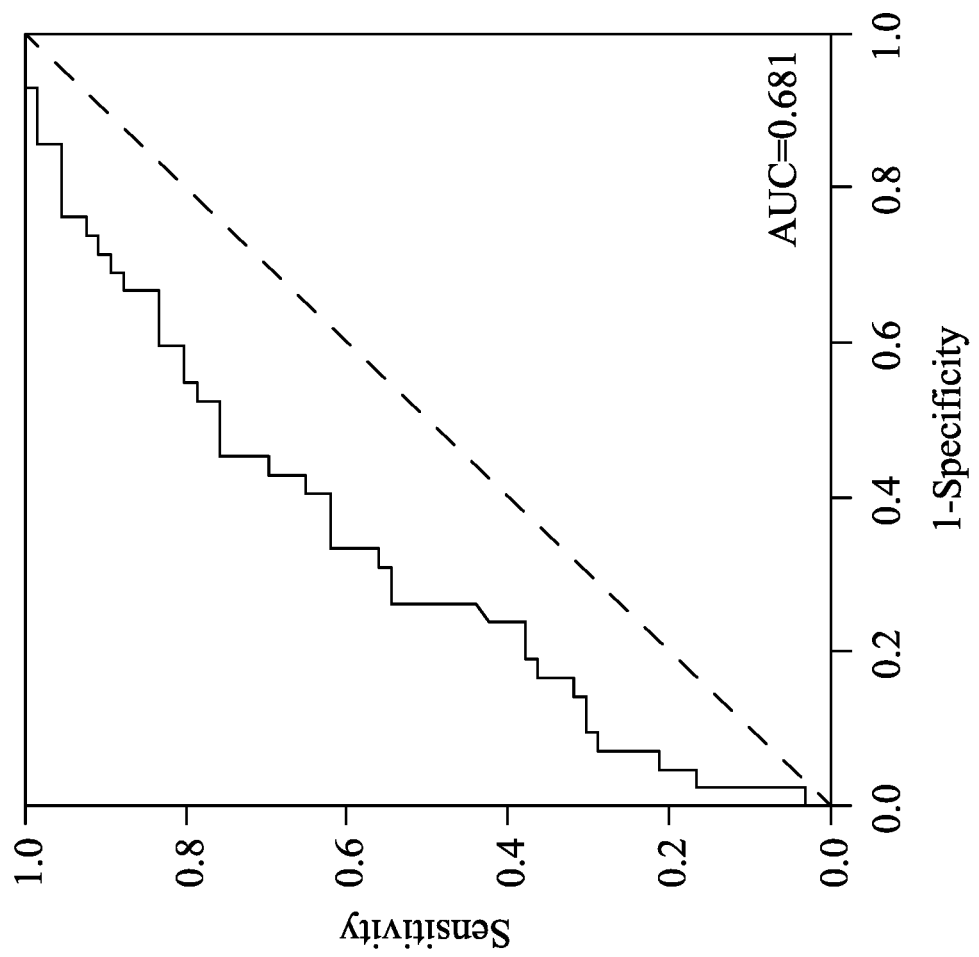

Specification includes a Sequence Listing.

(56) References Cited

FOREIGN PATENT DOCUMENTS

WO    WO-2016001907 A1 * 1/2016 ............. A61K 39/39

OTHER PUBLICATIONS

Honsawek et al., "Increased serum levels of serum hyaluronan in patients with dengue infection," J. Infect 54: 225-229 (Year: 2007).*
Al-Araimi et al., "Dengue Haemorrhagic Fever presenting as Acute Abdomen," SQU Med J vol. 11, Issue 2: 265-268 (Year: 2011).*
Aguiar et al., "Are we modelling the correct dataset? Minimizing false predictions for dengue fever in Thailand," Epidemiol. Infect. 142: 2447-2459 (Year: 2014).*
Tang TH et al. "Increased Serum Hyaluronic Acid and Heparan Sulfate in Dungue Fever: Association with Plasma Leakage and Disease Severity" Sci. Rep. vol. 7, Apr. 10, 2017, pp. 1-9.
Nathan, Michael et al., "Dengue Guidelines for Diagnosis, Treatment, Prevention and Control", 2009, World Health Organization, ISBN 978 92 4 154787 1.
Lin, Chun-Yu, et al., "Increased plasma hyaluronan levels correlate with the severity of Dengue virus infection—characterization of the molecular mechanisms involved", 6th FEBS Advanced Lecture Course (FEBS-MPST 2017)—Matrix Pathobiology, Signaling and Molecular Targets. May 25-30, 2017. p. 121.

* cited by examiner

Fig. 5

METHOD FOR TREATING SUBJECT SUFFERING FROM FLAVIVIRUS INFECTION

CROSS REFERENCE TO RELATED APPLICATIONS

This application is a continuation-in-part of U.S. patent application Ser. No. 15/881,350, which was filed Jan. 26, 2018 and claims the benefit of Taiwan Patent Application No. 106134411, filed Oct. 5, 2017, both of which are incorporated by reference as if fully set forth.

The sequence listing filed herewith, titled Sequence Listing, and having a file size of 1,049 bytes, is incorporated by reference as if fully set forth.

FIELD

The present invention is related to methods for treating Flavivirus infection, in particular to Flavivirus infectious illness including yellow fever, Japanese encephalitis, dengue fever, West Nile fever and Zika virus infection.

BACKGROUND

The viruses in the Flaviviridae family are single-stranded linear RNA viruses. Humans and other mammals are their natural hosts, and the viruses are spread widely via arthropods (e.g. ticks and mosquitoes). The Flaviviridae family is classified into four genera, including Flavivirus, Pestivirus, Hepacivirus and Pegivirus, and over 100 species. The Flavivirus genus includes the well-understood yellow fever virus, Japanese encephalitis virus (JEV), dengue virus, West Nile virus and Zika virus. The Pestivirus genus includes bovine viral diarrhea virus. The Hepacivirus genus is classified into 14 species which are abbreviated as the hepatitis viruses A, B, C . . . through N, wherein the well-known one is the hepatitis C virus. The Pegivirus genus is classified into 11 species which are abbreviated as the hepatotropic viruses A, B, C . . . through K.

Dengue fever, which mainly occurs in the subtropical and tropical countries, is an acute infectious disease caused by the dengue virus, and spread to humans via mosquitoes, e.g. *Aedes aegypti* and *Aedes albopictus*. The dengue viruses are classified into four types, i.e. I, II, III and IV, according to different virus serotypes, and each serotype has the abilities of infection and pathogenesis.

The latency period for the dengue fever is typically about 3 days to 8 days (the longest one being up to 14 days). The period between the day before illness and five days after illness is called "the communicability period" or "viremia". Dengue viruses exist in the patient's blood. Mosquitoes, *A. aegypti* or *A. albopictus*, will take up the dengue viruses if the patients are bitten by the mosquitoes during the communicability period. The dengue viruses enrich inside the mosquitoes during an 8-to-12-day multiplication, and the mosquitoes bite other people causing the dengue viruses to spread.

Some patients have mild syndromes during the dengue fever infection, and some do not even appear to show any symptoms. The typical symptoms of dengue fever include the phenomena such as a sudden fever higher than 38° C., headache, posterior eye pain, muscle soreness, arthralgia, rash, drowsiness, restlessness, liver enlargement, the increased vascular permeability, plasma leakage, bleeding, severe lethal bleeding and so on. Furthermore, if patients are infected with different dengue virus serotypes (DENV) for a consecutive two times, in particular the patients who are infected with the DENV-1 firstly followed by the DENV-2 or DENV-3 infection, or the patients who are infected with the DENV-3 firstly followed by the DENV-2 infection, the possibility of causing the dengue hemorrhagic fever (DHF) and dengue shock syndrome (DSS) is significantly increased to result in more severe clinical syndromes, such as shock or severe complications. Mortality is up to more than 20% if timely treatment is absent.

There is no sovereign remedy for treating dengue fever. In the prevention of dengue fever, Sanofi Pasteur (Lyon, France) developed the first dengue fever vaccine (a tetravalent attenuated live vaccine) in the world for people between the ages of 9 to 45 years old. However, this vaccine generated poor protection against DENV-2. In addition, GlaxoSmithKline (GSK, Brentford, the United Kingdom) also developed a deactivated vaccine, TDEN-PIV, that progressed to phase II clinical trials.

The World Health Organization (WHO) classified dengue fever patients into groups A, B and C depending on the occurrence of "warning sign" or not (*Dengue Guidelines for Diagnosis, Treatment, Prevention and Control*, 2009, World Health Organization, ISBN 978 92 4 154787 1), rather than the simple and traditional classification for dengue fever patients and DHF patients. The warning sign means that a dengue fever patient shows abdominal pain or abdominal tenderness, persistent vomiting, clinical fluid accumulation (e.g. ascites, pleural effusion and so on), mucosal bleed, lethargy, restlessness, the liver enlargement more than 2 cm, an increase in the hematocrit (HCT) concurrent with a rapid decrease in the platelet count, while keeping in mind co-existing conditions (e.g. diabetes, renal failure, chronic hemolytic disease, obesity, pregnancy, infancy, and old age), and adverse social circumstances (such as living alone, or living far from hospital).

Among these, patients in group A do not have neither "warning signs", co-existing conditions nor adverse social circumstances; patients in group B have "warning signs", and have the features of co-existing conditions and/or adverse social circumstances; and patients in group C have severe plasma leakage with shock and/or fluid accumulation with respiratory distress, severe bleeding, and/or organ impairment (such as liver function impairment, central nervous system impairment, heart failure, renal failure, cardiomyopathy, encephalopathy, encephalitis and so on).

In the treatment, the patients in group A are monitored at home for disease progression; the patients in group B accept hospitalization; and the patients in group C need an emergency remedy or are transferred to the hospital with good equipment and experienced physicians and nurses.

The classification of dengue cases by the WTO (2009 Edition) was established to provide appropriate triage to assist the clinical remedy, so as to study the mechanism of the disease and evaluate medical intervention (such as intravenous dehydration, new anti-virus drugs and vaccines and so on) in the future.

In addition to assisting doctors to evaluate the subsequent illness course of patients with a Flavivirus infectious illness at his/her early stage of illness so as to adopt the appropriate treatment or therapy, there is also a need for a therapy that can effectively treat the Flavivirus infectious illness, especially the dengue fever.

It is therefore the Applicant's attempt to deal with the above situation encountered in the prior art.

SUMMARY

To provide an effective treatment for the Flavivirus infectious illness, novel and progressive techniques are developed in the present invention. The present invention discloses methods for effectively relieving and treating Flavivirus infection by blocking a hyaluronan in a serum of a subject.

One object of this application is to provide a method for treating a subject suffering from a Flavivirus infection. The method includes a step of administering to the subject a pharmaceutical composition including a pharmaceutically effective amount of an anti-CD44 antibody.

In one embodiment, the Flavivirus infection causes the subject to have an illness including yellow fever, Japanese encephalitis, dengue fever, West Nile fever or a Zika virus infection. In one embodiment, the subject is a mammal.

In one embodiment, the subject has a level of a hyaluronan in a serum, and the level is higher than or equal to 70 ng/mL to indicate that a warning sign will occur in an illness course of the subject. In one embodiment, the warning sign includes abdominal pain or abdominal tenderness, persistent vomiting, clinical fluid accumulation, mucosal bleed, lethargy, restlessness, liver enlargement of more than 2 centimeters (cm), and the increase in a hematocrit (HCT) concurrent with a rapid decrease in a platelet count.

In one embodiment, the pharmaceutical composition further includes a pharmaceutically acceptable carrier, an excipient, a diluent, or an adjuvant.

In one embodiment, the pharmaceutical composition further includes 4-methyl umbelliferone sodium salt, CD44 small interfering RNA (siRNA) or hyaluronidase, and the CD44 siRNA is one selected from the group consisting of an SEQ ID NO:1, an SEQ ID NO: 2, an SEQ ID NO: 3, an SEQ ID NO: 4 and the combination thereof.

According to the present invention, the pharmaceutically effective amount is in a range from 1 mg/kg to 20 mg/kg, preferably from 4 mg/kg to 8 mg/kg.

The present invention further discloses a method for treating a subject suffering from a Flavivirus infection, including: administering to the subject a pharmaceutical composition including a first pharmaceutically effective amount of an anti-CD44 antibody, and subsequently administering to the subject the pharmaceutical composition including a second pharmaceutically effective amount of the anti-CD44 antibody.

In one embodiment, the first pharmaceutically effective amount is equal to the second pharmaceutically effective amount, and the anti-CD44 antibody with the second pharmaceutically effective amount is administered at least 24 hours after the anti-CD44 antibody with the first pharmaceutically effective amount was administered.

BRIEF DESCRIPTION OF THE DRAWINGS

The objectives and advantages of the present invention will become more readily apparent to those ordinarily skilled in the art after reviewing the following detailed descriptions and accompanying drawings.

FIG. 1 illustrates a diagram showing a receiver operating characteristic (ROC) curve for the level of serum hyaluronan (SA) of the dengue fever patients at the early stage of the illness in the present invention.

FIG. 2 illustrates a diagram showing the ratio of the warning signs (WS)-positive to WS-negative in the dengue fever patients during their whole illness courses in the present invention.

FIG. 3 illustrates a diagram showing the platelet (PLT) nadir (smaller than or not smaller than 50,000/μl) of the dengue fever patients during their whole illness courses in the present invention.

FIG. 4 illustrates a diagram showing the blood concentration phenomenon for the increased hematocrit (HCT) level (>20%) appearing in the dengue fever patients during their whole illness courses in the present invention.

FIG. 5 illustrates a diagram showing the Akt phosphorylation in the human vascular endothelial cells being subjected to the dengue virus (DENV) nonstructural protein 1 (NS1) or the pharmaceutical composition of the present invention.

FIG. 6 illustrates a diagram showing the transwell permeability assay of human microvascular endothelial cells.

FIG. 7 illustrates an experimental protocol of an animal model.

FIG. 8 illustrates a diagram showing the body weight changes in different groups of the animal model from Day 0 to Day 5.

DETAILED DESCRIPTION OF THE PREFERRED EMBODIMENTS

The present invention will now be described more specifically with reference to the following embodiments. It is to be noted that the following descriptions of the preferred embodiments of this invention are presented herein for purpose of illustration and description only; they are not intended to be exhaustive or to be limited to the precise form disclosed.

Definition

The term "Flavivirus" herein refers to the viruses which include, but are not limited to, yellow fever virus, Japanese encephalitis virus (JEV), dengue virus, West Nile virus and Zika virus.

The illnesses of the dengue fever patients herein are classified into "dengue fever", "severe dengue", "dengue hemorrhagic fever (DHF)", "dengue shock syndrome (DSS)" and so on according to the clinical manifestations or examination results.

The definition of the term "severe dengue" herein conforms to one or more items as follows: severe plasma leakage with shock, severe plasma leakage with fluid accumulation and respiratory distress, severe bleeding evaluation, severe organ impairment, glutamic oxaloacetic transaminase (GOT) or glutamic pyruvic transaminase (GPT)≥1,000 IU/L in the liver, consciousness impairment in the central nervous system, heart failure or others.

According to the classification of the dengue cases by the WHO (2009 Edition), the term "warning sign" herein is defined as that dengue fever patients show abdominal pain or abdominal tenderness, persistent vomiting, clinical fluid accumulation, mucosal bleeding, lethargy, restlessness, liver enlargement of more than 2 cm, and an increase in the hematocrit (HCT) concurrent with a rapid decrease in the platelet count.

The term "yellow fever" herein means an illness that a subject is infected with the yellow fever virus, and the symptoms of the yellow fever include fever, abnormal liver functions, outbreak of chills, headache, backache, muscle pain throughout the body, anorexia, poor appetite, vomiting, and so on. A number of yellow fever patients enter into a poisoning stage after a relief for several hours to one day, and the symptoms such as fever, icterus, albuminuria and bleeding occurs. Even, liver or renal failure occurs to cause anuria (anuresis).

The term "Japanese encephalitis" herein means an illness that a subject is infected with the Japanese encephalitis virus (JEV), and the symptoms of the Japanese encephalitis includes fever, diarrhea, headache or vomiting. The clinical manifestation of the patients with mild symptoms is aseptic meningitis or the fever of unknown origin, and the severe patients show the worsening consciousness conditions, general weakness, high fever, partial neurological disability, dyskinesia, Parkinson's syndrome, obnubilation, coma or death.

The term "West Nile fever" herein means an illness that a subject is infected with the West Nile virus, and the symptoms include fever, headache, fatigue, arthralgia, muscle pain, rash, lymphatic enlargement, gastrointestinal disorder. The severe patients have symptoms such as cephalomeningitis, encephalitis, acute asthenic paralysis syndrome and so on.

The term "Zika virus infection" herein means an acute infection that a subject is infected with the Zika virus, and its latency period is about 3 days to 7 days (the longest one being up to 12 days). The classic symptoms are fever with rash, arthralgia or conjunctivitis (pinkeye), headache, muscle pain, posterior eye pain and so on, and even the nervous system complications (such as Guillain-Barre syndrome (GBS)) or immune system complications (such as idiopathic thrombocytopenic purpura (ITP)) may occur. If a pregnant woman is infected with Zika virus, she may deliver a newborn with neurological abnormality (such as microcephaly).

In the embodiment of the present invention, the patients who are infected with dengue virus and identified to have dengue fever are the population, and the levels of hyaluronan in the sera of the patients are measured and statistically calculated to define that the warning sign will occur in the illness course of the patients when the level is higher than or equal to 70 ng/mL. Because the diseases caused by the yellow fever virus, JEV, West Nile virus and Zika virus (where all belong to the Flavivirus) also make patients have symptoms similar to dengue fever, the technique in the present invention can also be used in patients who suffer from yellow fever, Japanese encephalitis, West Nile fever and Zika virus infection.

Embodiment 1

Experimental Methods:

To determine whether a warning sign will occur in a patient with a Flavivirus infectious illness, the level of SA in the patient was determined using the Hyaluronan DuoSet® ELISA development system (Cat. No. DY3614-05, R&D systems, Inc., U.S.A.). The skilled person in the art can implement Embodiment 1 in view of the manufacturer's instructions of the Hyaluronan DuoSet® ELISA development system, or perform the experiments by preparing the materials and reagents by himself/herself and using the same experimental methods.

First, a 96-well microplate for the enzyme-linked immunosorbent assay (ELISA) was prepared as follows. The hyaluronan capture reagent (i.e. recombinant human aggrecan) was diluted to a working concentration in the phosphate-buffered saline (PBS, 137 mM NaCl, 2.7 mM KCl, 8.1 mM $Na_2HPO_4$, 1.5 mM $KH_2PO_4$, pH 7.2-7.4, 0.2 µm filtered) without carrier protein. The 96-well microplate with 100 µL per well of the diluted hyaluronan capture reagent was immediately coated. The microplate was sealed and incubated overnight at room temperature.

Each well was aspirated and washed with a wash buffer (0.05% Tween® 20 in PBS, pH 7.2-7.4), the process was repeated two times for a total of three washes. In detail, each well was washed by filling with the wash buffer (400 µL) using a squirt bottle, a manifold dispenser or an autowasher. Complete removal of liquid at each step was essential for good performance. After the last wash, any remaining wash buffer was removed by aspirating or by inverting the microplate and blotting it against clean paper towels. The microplate was blocked by adding 300 µL of a reagent diluent (5% Tween® 20 in PBS, pH 7.2-7.4, 0.2 µm filtered) to each well. The microplate was incubated at room temperature for a minimum of 1 hour. The aspiration/wash was repeated. The microplate was now ready for the sample addition and the ELISA experiment.

A 100-µL sample or hyaluronan standards in the reagent diluent (or an appropriate diluent) per well was added to the well. An adhesive strip was covered on the microplate, and the microplate was incubated for 2 hours at room temperature. The aspiration/wash was repeated. A 100-µL biotinylated detection reagent (i.e. the biotinylated recombinant human proteoglycan) which was diluted in the reagent diluent was added to each well. A new adhesive strip was covered on the microplate, which was further incubated for 2 hours at room temperature. A 100-µL working dilution of streptavidin-horseradish peroxidase (HRP) was added to each well. The microplate was covered and incubated for 20 minutes at room temperature. Placing the microplate in direct light was avoided. The aspiration/wash was repeated. A 100-µL substrate solution (1:1 (v/v) mixture of color reagent A ($H_2O_2$) and color reagent B (tetramethylbenzidine)) was added to each well, and the microplate was incubated for 20 minutes at room temperature. Placing the microplate in direct light was avoided. A 50-µL stop solution (2 N $H_2SO_4$) was added to each well. The microplate was gently tapped to ensure thorough mixing. The optical density of each well was determined immediately using a microplate reader set to 450 nm.

A six point standard curve of the hyaluronan standard using 3-fold serial dilutions in the reagent diluent was recommended. Thus, the concentration of the hyaluronan standard was 90, 30, 10, 3.33, 1.11 and 0.370 ng/mL. A standard curve was plotted based on the concentration of the hyaluronan standard and its average optical density.

Experimental Results:

Please refer to FIG. 1, which illustrates a diagram showing a receiver operating characteristic (ROC) curve for the level of SA in the dengue fever patients at the early stage of the illness in the present invention. When the serum sample of each dengue fever patient (n=108) was measured, a critical value whether the warning sign will occur was precisely determined by the ROC curve depending on whether the patients show the warning sign. As shown in FIG. 1, an area under curve (AUC) is 0.681 (95% confidence interval (C.I.)=0.58-0.78, p value=0.002), the best critical value is 70.06 ng/mL, the sensitivity is 0.758, and the 1-specificity is 0.548. Therefore, in the subsequent analysis, the level of SA which is higher than or equal to 70 ng/mL is the critical value for determining whether the warning sign will occur in the whole illness course of the patient.

Please refer to Table 1, which is the univariate analysis of factors associated with the dengue fever patients presented with warning signs (WS) throughout the illnesses (n=108). The levels of hyaluronan in the sera of the dengue fever patients (n=108) were measured during the febrile phase (at early illness stage), and their illness progression was traced until recovery. If the level of SA in the dengue fever patient is higher than or equal to 70 ng/mL during the febrile phase, the possibility that they show "the warning sign" in whole illness course is 3.78 times higher than the patients with the level lower than 70 ng/mL (p=0.003, 95% C.I.=1.65-8.66). The results of the univariate analysis in Table 1 also showed that the age ≥65 years, the secondary dengue viral infection, and the level of SA≥70 ng/mL (at the febrile phase) are prediction factors for predicting whether the dengue fever patients belong to the "WS-positive" group. Furthermore, important prediction factors (i.e. patient's age, and secondary infection) were calibrated using multivariate analysis, and the results still showed that the level of SA≥70 ng/mL in the dengue fever patient at the early stage (the febrile phase) is an independent prediction factor for predicting whether the warning sign will occur in the illness course of the patient (referring to Table 2). Therefore, depending on the level of SA (≥ or <70 ng/mL) in the dengue fever patient at the early illness stage, doctors can determine whether the warning sign will occur in his/her illness course, and further evaluate the patient's subsequent conditions so as to provide him/her with the appropriate remedy or treatment.

TABLE 1

Univariate analysis of factors associated with dengue fever patients presented with warning signs (WS) throughout the illnesses (n = 108)

| Variables | No. (%) of patients WS-positive (n = 66) | No. (%) of patients WS-negative (n = 42) | Odds ratio (95% Confidence interval) | p-value |
|---|---|---|---|---|
| Demographic characteristics | | | | |
| Gender, female | 35 (53.0) | 19 (45.2) | 1.37 (0.63-2.97) | 0.554 |
| Age ≥65 years | 34 (51.5) | 10 (23.8) | 3.40 (1.44-8.02) | 0.008 |
| Secondary infection | 43 (65.2) | 17 (40.5) | 2.75 (1.24-6.10) | 0.020 |
| Comorbidities | | | | |
| Diabetes | 16 (24.2) | 7 (16.7) | 1.60 (0.60-4.30) | 0.486 |
| Laboratory data | | | | |
| Thrombocytopenia (first sampling) | 26 (39.4) | 11 (26.2) | 1.83 (0.79-4.27) | 0.230 |
| SA (febrile phase) ≥70 ng/ml | 50 (75.8) | 19 (45.2) | 3.78 (1.65-8.66) | 0.003 |

TABLE 2

Multivariate analysis of the serum samples of the dengue fever patients (n = 108)

| Variable | Adjusted odds ratio (95% CI) | p-value |
|---|---|---|
| Age ≥65 years | 2.01 (0.78-5.21) | 0.151 |
| Secondary infection | 2.00 (0.84-4.76) | 0.118 |
| Serum HA (febrile phase) ≥70 ng/ml | 2.80 (1.15-6.80) | 0.023 |

Figure 2:
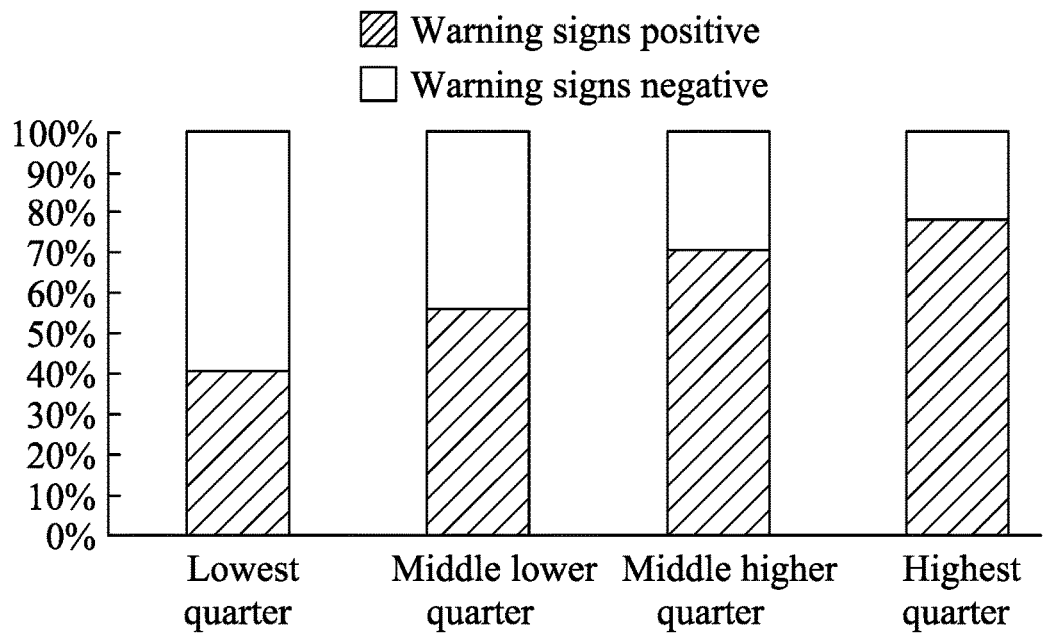
Figure 3:
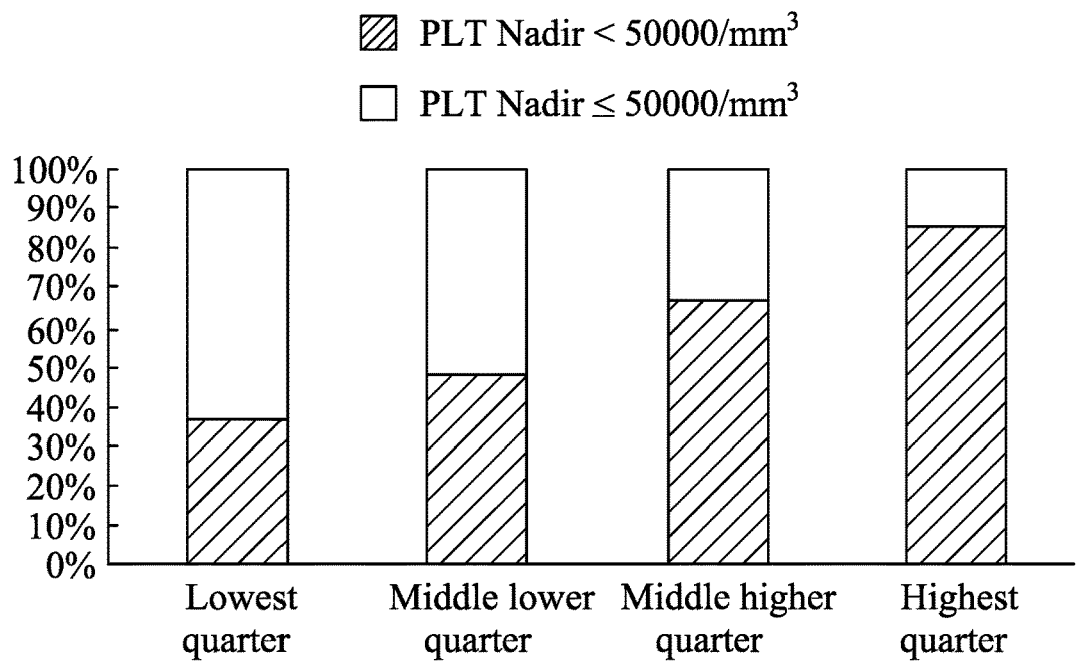
Figure 4:
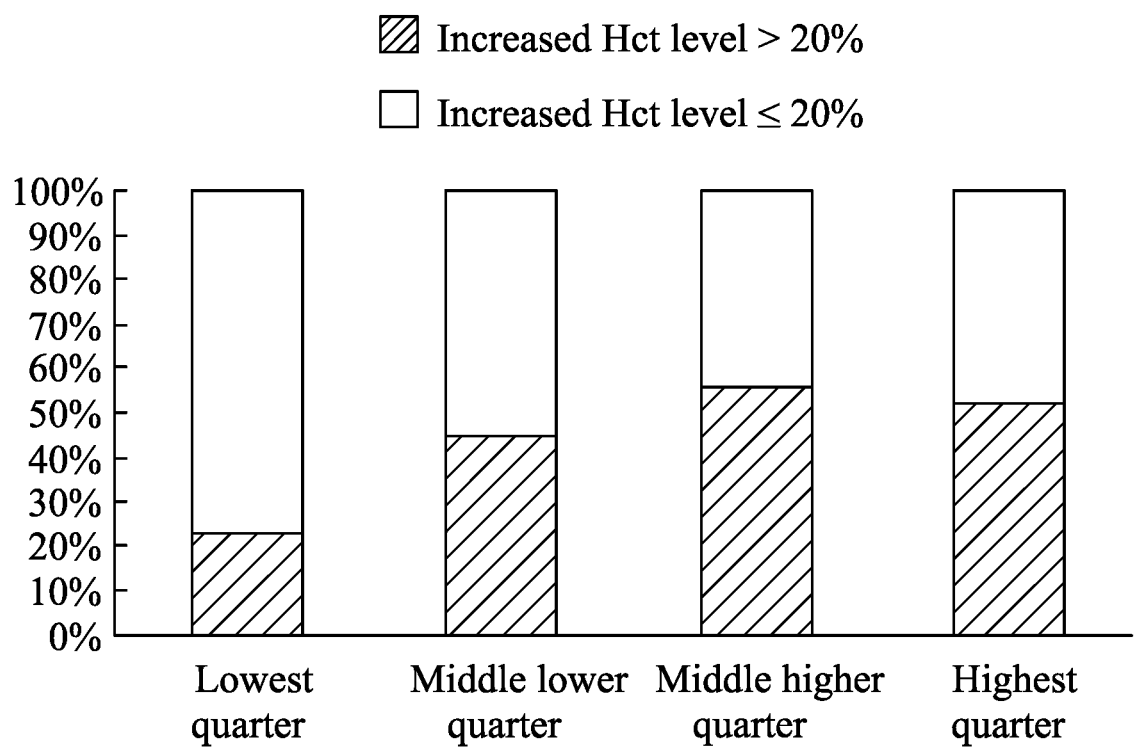

Please refer to FIG. 2 to FIG. 4, which illustrates diagrams showing (a) the ratio of the warning signs (WS)-positive to the WS-negative, (b) the platelet (PLT) nadir (< or ≥50,000/μl), and (c) the blood concentration phenomenon for the increased hematocrit (HCT) level (>20%) in the dengue fever patients during their whole illness course in the present invention. These 108 dengue fever patients were classified into four groups (i.e. lowest quarter, middle lower quarter, middle higher quarter, and highest quarter) depending on the levels of SA at their early illness stage (the febrile stage). It can be known from FIGS. 2 to 4 that, compared to the group with the lower level of SA, the group with the higher level of SA has a high possibility of having the warning sign in the whole illness course, and the PLT nadir <50,000/μl and the increased hematocrit (HCT) level (>20%).

Embodiment 2

Figure 5:
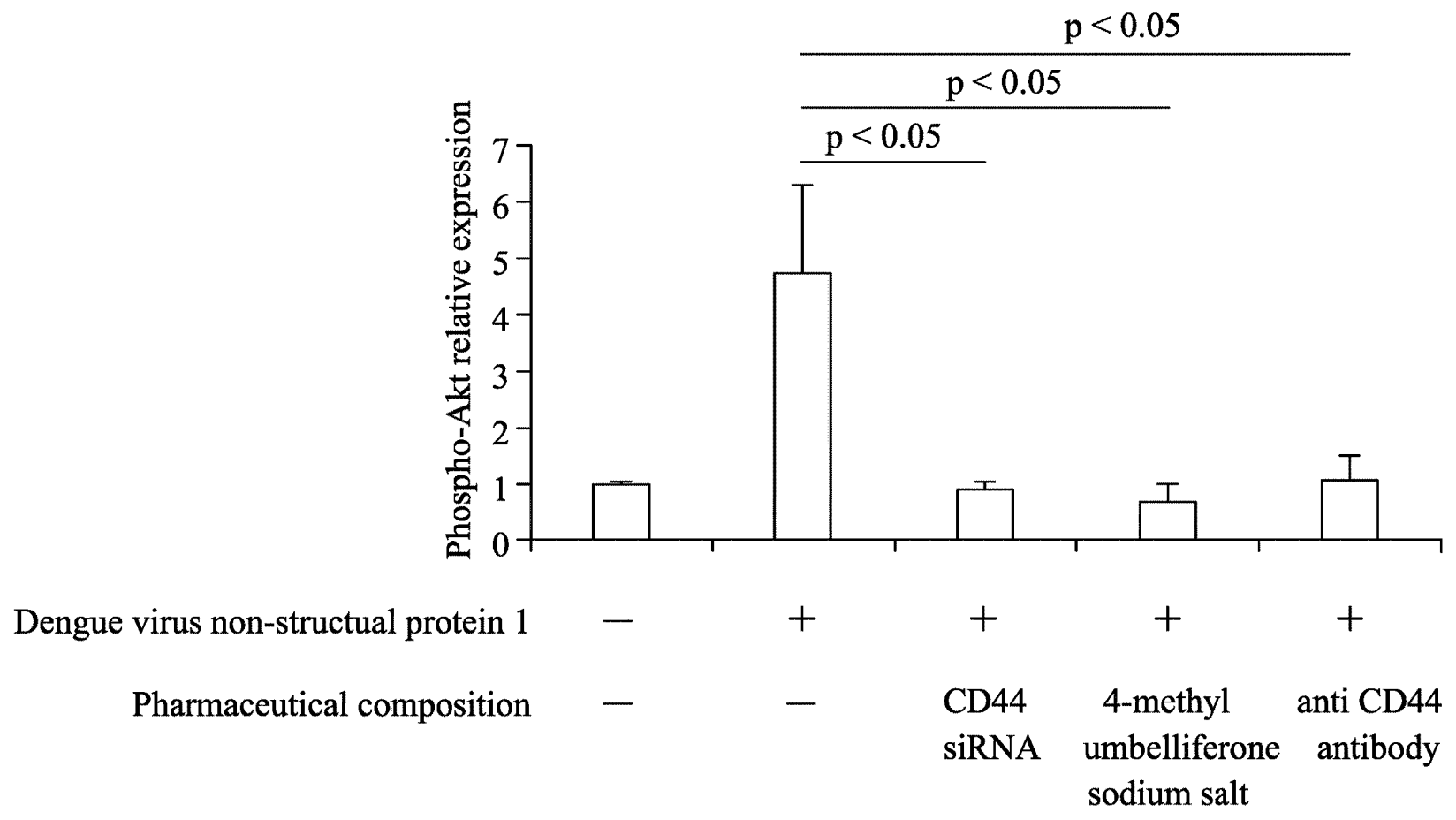

Based on whether the warning sign will occur in the illness course of the patent with the level of SA≥70 ng/mL, a pharmaceutical composition for blocking the SA in the patient to prevent inflammation is disclosed in this Embodiment. The pharmaceutical composition includes a pharmaceutically effective amount of 4-methyl umbelliferone sodium salt, wherein the therapeutically effective amount is an effective blood concentration of 4-methyl umbelliferone sodium salt of the patient being in a range from 0.05 mM to 5 mM. The pharmaceutical composition may further include a pharmaceutically acceptable carrier, an excipient, a diluent, or an adjuvant. Please refer to FIG. 5, which illustrates a diagram showing the Akt phosphorylation in the human vascular endothelial cells being subjected to the dengue virus (DENV) nonstructural protein 1 (NS1) or the pharmaceutical composition of the present invention. In FIG. 5, the human vascular endothelial cells ($4 \times 10^5$ cells cultivated in a 60-mm dish) were treated with a nonstructural protein 1 (3 μg/ml, Cat. No. ENZ-PRT105-0100, Enzo Life Sciences, Inc., NY, U.S.A.), and the Akt phosphorylation was significantly induced in the cells, indicating that the dengue virus results in inflammation in the human vascular endothelial cells. In addition, the human vascular endothelial cells were treated with 4-methyl umbelliferone sodium salt for 12 hours followed by the DENV NS1 treatment. Subsequently, the cellular proteins were extracted and subjected to the sodium dodecyl sulfate polyacrylamide gel electrophoresis (SDS-PAGE) to separate the proteins according to their molecular weights. Next, the proteins in the gel were transferred to a polyvinylidene difluoride (PVDF) membrane, and the phospho-Akt (p-Akt) signal on the PVDF membrane was detected using the Western blotting and the p-Akt antibody. The results showed that a range from 0.05 mM to 5 mM is the effective blood concentration of 4-methyl umbelliferone sodium salt in the dengue fever patient, indicating that 4-methyl umbelliferone sodium salt can be used to inhibit the inflammation of the human vascular endothelial cells caused by the dengue virus (referring to FIG. 5).

Embodiment 3

The CD44 antigen, which plays important roles in many biological functions (such as inflammation), is a surface glycoprotein on mammalian cells, and hyaluronan is a main molecule to bound with the CD44 antigen. Thus, an abundance of hyaluronan would bind to CD44 to influence CD44's biological functions when the level of SA in the dengue fever patient is too high. In this Embodiment, CD44 small interfering RNA (siRNA) was used to inhibit the CD44 expression of the vascular endothelial cells of the dengue fever patients, and block the combination between hyaluronan and CD44. In this Embodiment, the experimental method for inhibiting cellular protein expression using siRNA was known to the skilled person in the art, and the CD44 siRNAs were the artificially synthesized SEQ ID NO:1 (5'-GAAUAUAACC UGCCGCUUU-3'), SEQ ID NO: 2 (5'-CAAGUGGACU CAACGGAGA-3'), SEQ ID NO: 3 (5'-CGAAGAAGGU GUGGGCAGA-3') and SEQ ID NO: 4 (5'-GAUCAACAGU GGCAAUGGA-3'). Furthermore, two, three or four siRNAs in the SEQ ID NOs: 1 to 4 may be combined to inhibit the CD44 expression of the vascular endothelial cells (4×10⁵ cells cultivated in a 60-mm dish) of the dengue fever patient. First, in view of the manufacturer's instructions of siLentFect™ Lipid Reagent (Bio-Rad laboratories AB, Sweden), the CD44 siRNA was mixed with siLentFect™ Lipid Reagent, the mixture was transfected into the human vascular endothelial cells for 24 hours followed by the DENV NS1 treatment (3 µg/ml, Cat. No. ENZ-PRT105-0100, Enzo Life Sciences, Inc., NY, U.S.A.). Subsequently, the cellular proteins were extracted and subjected to the SDS-PAGE to separate the proteins according to their molecular weights. Next, the proteins in the gel were transferred to a PVDF membrane, and the p-Akt signal on the PVDF membrane was detected using the Western blotting and the p-Akt antibody. The results showed that a range from 1 nM to 100 nM is an effective blood concentration of CD44 siRNA (SEQ ID NOs: 1 to 4) in the dengue fever patient, indicating that the CD44 siRNA can be used to inhibit the inflammation of the vascular endothelial cells in humans caused by the dengue virus (referring to FIG. 5). Therefore, the CD44 siRNA (SEQ ID NOs: 1 to 4) of the present invention can be used to prepare a pharmaceutical composition for treating inflammation in dengue fever patients.

Embodiment 4

In this Embodiment, an anti-CD44 antibody (MA4400, Invitrogen, CA, U.S.A.) of 5 µg/ml to 500 µg/ml was used to inhibit the CD44 surface antigen of the vascular endothelial cells of the dengue fever patients. First, the human vascular endothelial cells (4×10⁵ cells cultivated in a 60-mm dish) were treated with the anti-CD44 antibody for 12 hours followed by the treatment of DENV NS1 (3 µg/ml, Cat. No. ENZ-PRT105-0100, Enzo Life Sciences, Inc., NY, U.S.A.). Subsequently, the cellular proteins were extracted and subjected to the SDS-PAGE to separate the proteins according to their molecular weights. Next, the proteins in the gel were transferred to a PVDF membrane, and the p-Akt signal on the PVDF membrane was detected using Western blotting and the p-Akt antibody. The results showed that a range from 5 µg/ml to 500 µg/ml is an effective blood concentration of anti-CD44 antibody in the dengue fever patient to inhibit p-Akt in the vascular endothelial cells of the dengue fever patients, indicating that the anti-CD44 antibody can be used to inhibit the inflammation of the vascular endothelial cells in humans caused by the dengue virus (referring to FIG. 5). Therefore, the anti-CD44 antibody of the present invention can be used to prepare a pharmaceutical composition for treating inflammation in dengue fever patients.

Embodiment 5

Vascular leakage is an important feature in several diseases, such as septic shock, viral hemorrhagic fever, cancer metastasis and ischemia-reperfusion injuries. Thus, an in vitro endothelial permeability assay will provide insight into the establishment or progression of such diseases. The transwell permeability assays directly detect the penetration of a specific molecule, which can be detected by a spectrometer-based absorbance reader.

Figure 6:
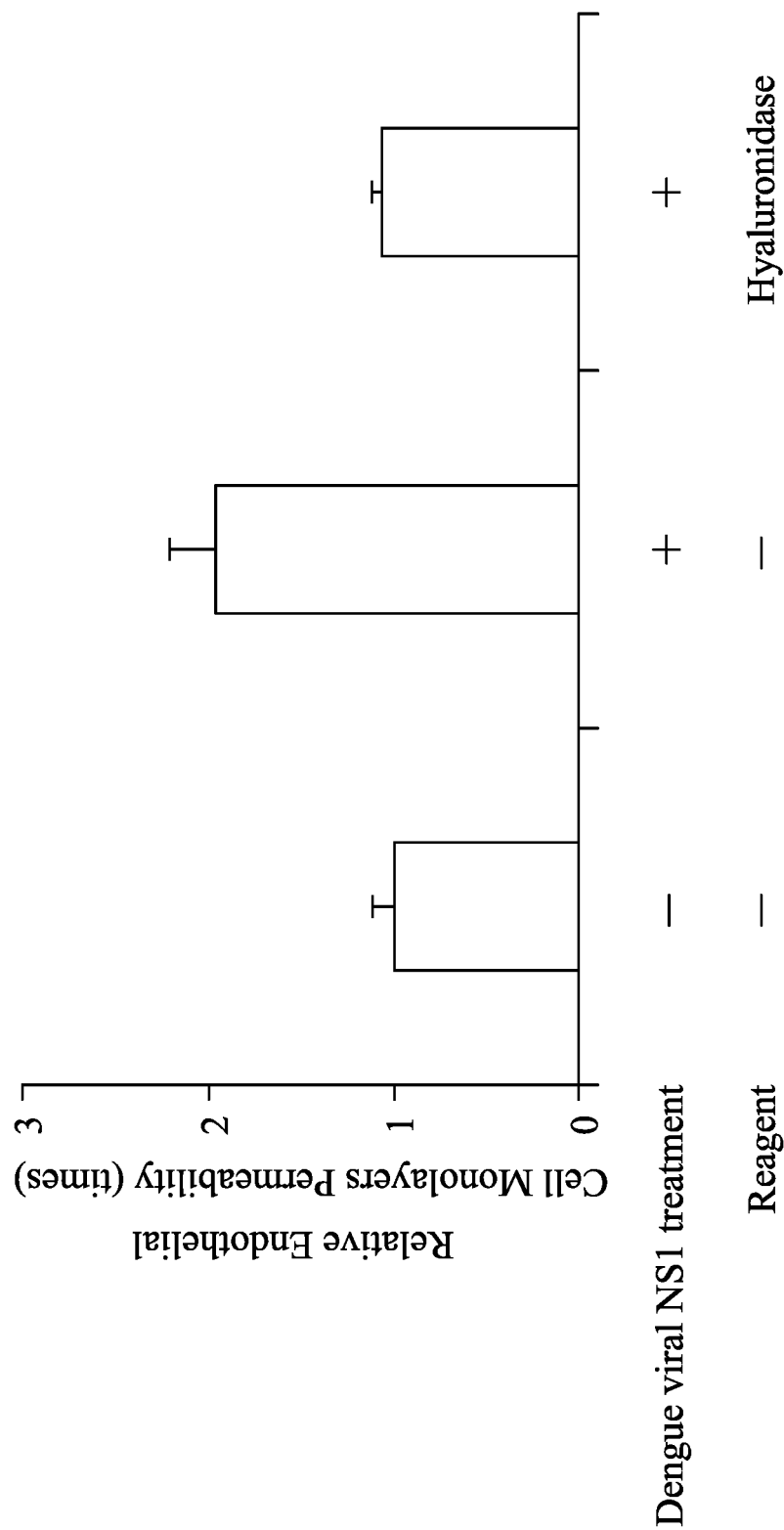

The permeability of human microvascular endothelial cells treated or not with DENV NS1 (3 µg/ml, Cat. No. ENZ-PRT105-0100, Enzo Life Sciences, Inc., NY, U.S.A.), was measured by an in vitro transwell permeability assay that mimics human endothelium in vivo (referring to http://www.bio-protocol.org/e2273). In brief, human microvascular endothelial cells (2×10⁵) were grown in a 24-Transwell® (pore size: 0.4 µm, Cat. No. 3414; Corning, Kennebunk, Me., U.S.A.) for 5 days until a confluent monolayer was formed. Next, some of the samples were treated for 6 hours with DENV NS1 protein in the absence or presence of exogenously added hyaluronidase (0.5 unit/mL to 50 units/mL), media was aspirated, and 200 µL fresh serum-free medium containing 3 µL of streptavidin-horseradish peroxidase (HRP) (GE Healthcare, Cat. No. RPN1231, UK) was added. To measure the HRP that had leaked through the endothelial layer, the inserts were moved to a new 24-well plate with 500 µl of serum-free medium, covered and placed in a 37° C. incubator for 5 minutes. Twenty microliters of medium, from each lower chamber, was transferred to a 96-well plate and analyzed for HRP activity by adding 100 µL 3,3',5,5'-tetramethylbenzidine (TMB) substrate (Sigma-Aldrich, Cat. No. T4444, St. Louis, Mo., U.S.A.). Color development was detected by an EnSpire Multimode Reader (PerkinElmer, Upplands Väsby, Sweden) at 450 nm. The results showed that the concomitantly added hyaluronidase could reverse the DENV NS1-induced endothelial hyperpermeability significantly (referring to FIG. 6).

Embodiment 6

From the results of the in vitro experiment, it is found that anti-CD44 antibody can inhibit the inflammation caused by DENV NS1 protein. To investigate whether the anti-CD44 antibody inhibits the dengue fever in an animal host, an animal model is established in the present invention. The model-specific experimental mice used in the present invention is AGB6 mice, which were C57BL/6 mice deficient in both type I IFN (IFN-α/β) receptor and type II IFN (IFN-γ) receptor, and were susceptible to dengue virus infection. Preferably, the AGB6 mice were infected by DENV-2 or DENV-4. All mice were maintained under SPF conditions in autoclaved IVC (Rungshin Plastic Industry Co., Ltd, Taichung, Taiwan, ROC), and the room condition under a temperature 23±2° C., a relative humidity of 40% to 60%, and a 12:12-h light:dark cycle.

Figure 7:
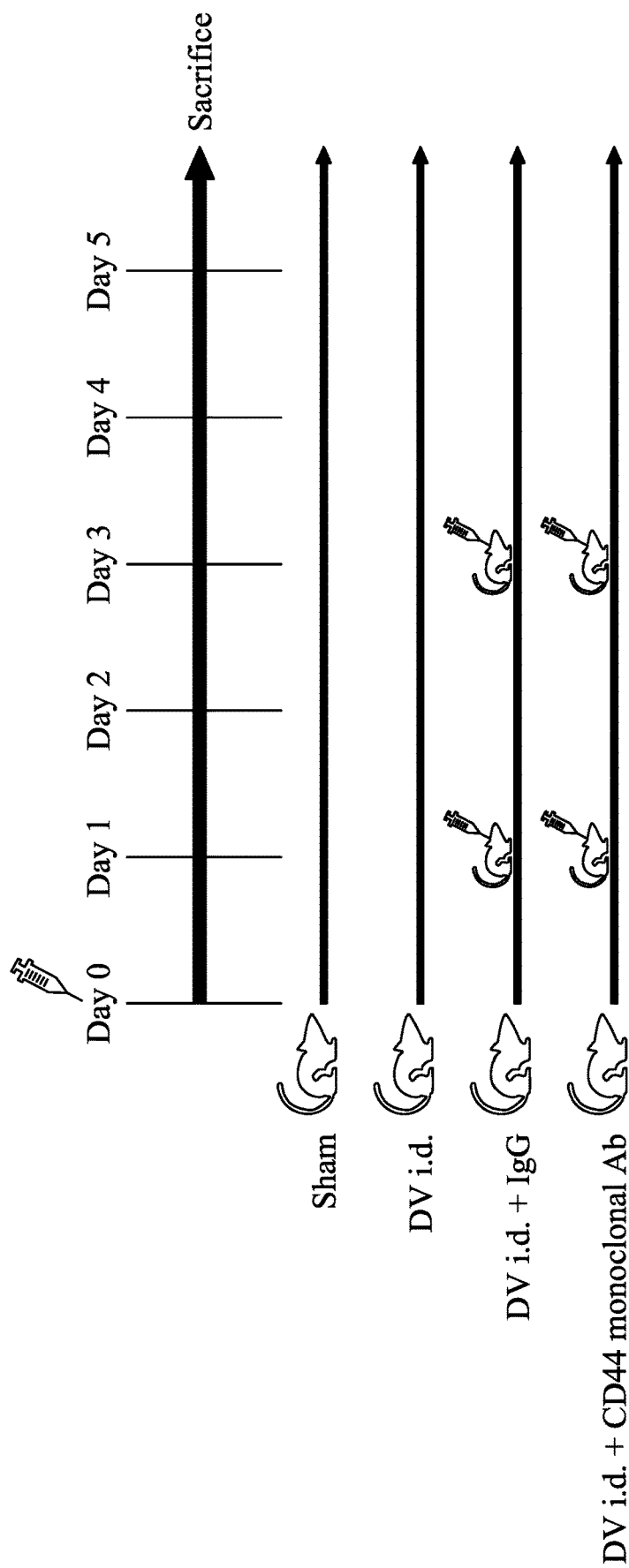

FIG. 7 shows the experimental protocol of the animal model. 2×10⁷ PFU of DENV-2 were dissolved in 200 µl of MEM (Minimum Essential Medium) to prepare a working solution for use in the animal model. Twelve 8-week old mice were randomly assigned into four groups: the Sham Group was injected with equal volume of medium without the dengue virus on Day 0 via intra-dermal (i.d.) injection, while DV, IgG and anti-CD44 antibody (anti-CD44 Ab) Groups were injected with 2×10⁷ PFU of DENV-2 per mouse on Day 0 via i.d. injection. Mice in IgG Group were injected with 6 mg/kg of IgG2b antibody at 24 and 72 hours post infection via intra-peritoneal (i.p.) injection, and the mice in anti-CD44 Ab Group were injected with 6 mg/kg of anti-CD44 monoclonal antibody at 24 and 72 hours post infection via i.p. injection. The changes of the mice's body weights in this experiment were recorded from Day 0 to Day 5.

Figure 8:
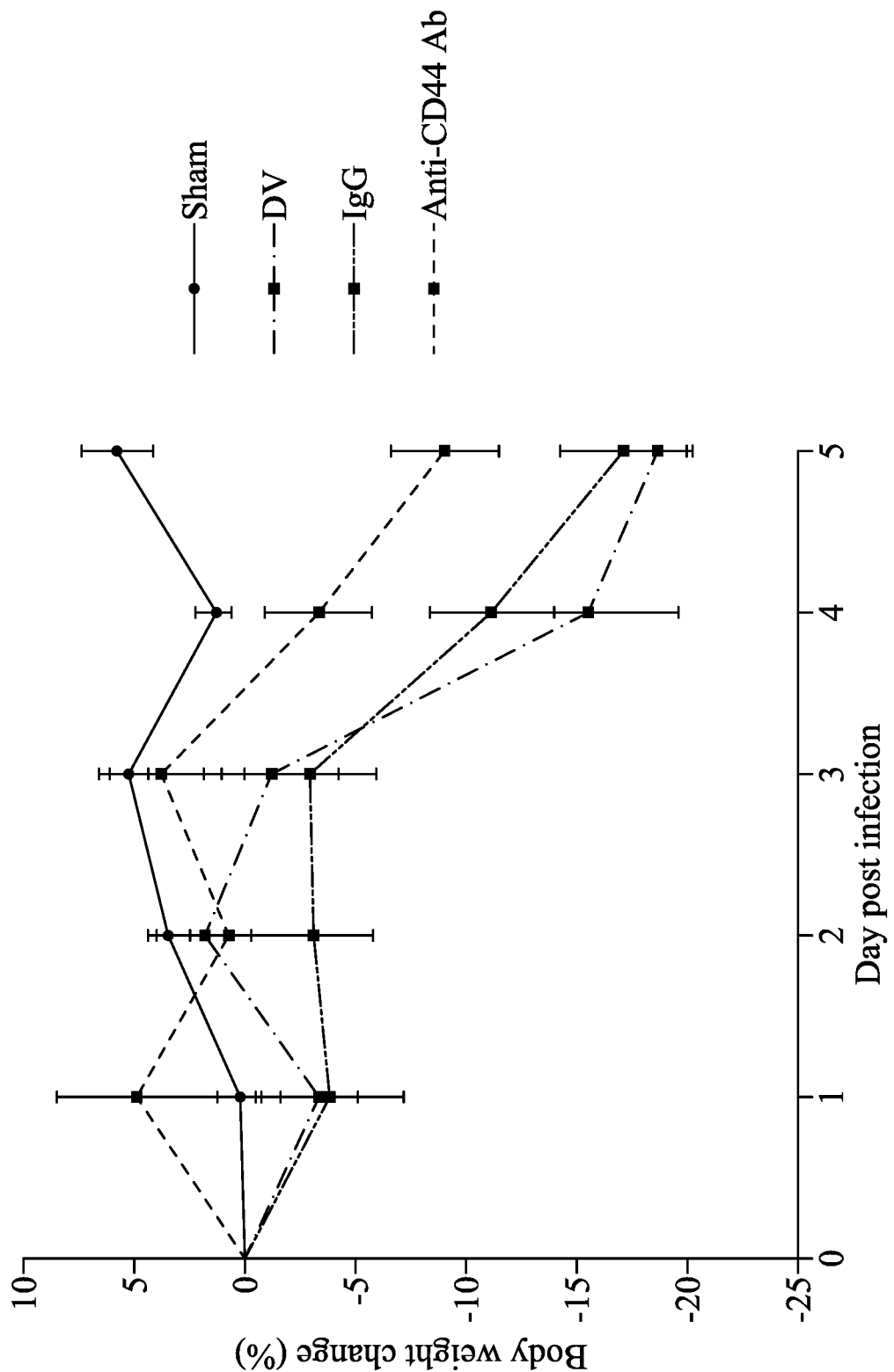

FIG. 8 shows the body weight changes in different groups of the animal model from Day 0 to Day 5. It can be known from FIG. 8 that the body weights in the mice of DV and IgG Groups decreased significantly after Day 3 when compared with Sham Group, indicating that DENV-2 infection causes lethality in these immunocompromised AGB6 mice. However, the mice in the anti-CD44 Ab Group revealed minor weight loss when compared with the DV and IgG Groups. It was exciting to find that the administration of the anti-CD44 monoclonal antibody achieves a better clinical outcome and a minor weight loss in the mice infected by the dengue virus, even though the anti-CD44 monoclonal antibody was administered 24 hours after the infection. These data suggest that anti-CD44 monoclonal antibody can inhibit excessive immune response in the dengue fever patients caused by abundant hyaluronan by blocking the combination between hyaluronan and CD44.

Based on the experimental data above, the present invention provides a method for treating a subject suffering from Flavivirus infection, including a step of administering to the subject a pharmaceutical composition including a pharmaceutically effective amount of an anti-CD44 antibody. In one embodiment, the Flavivirus infection causes the subject to have an illness being yellow fever, Japanese encephalitis, dengue fever, West Nile fever or Zika virus infection, and the subject is a mammal, especially human or murine. According to the present invention, the pharmaceutically effective amount of the anti-CD44 antibody for treating Flavivirus infection is in a range from 1 mg/kg to 20 mg/kg, preferably from 4 mg/kg to 8 mg/kg. According to the present invention, the pharmaceutical composition further includes 4-methyl umbelliferone sodium salt, CD44 siRNA, hyaluronidase or the combination thereof.

According to the animal model in the present invention, the present invention provides an additional method for treating a subject suffering from Flavivirus infection. In this method, the anti-CD44 monoclonal antibody was administered twice after the Flavivirus infection. Specifically, the anti-CD44 monoclonal antibody was administered at a first time point, and then subsequently administered at a second time point. Preferably, the second time point is at least 24 hours after the first time point. In one embodiment, the second time point is 48 hours after the first time point. In one embodiment, the amount of the anti-CD44 monoclonal antibody administered at the first time point is equal to that at the second time point. In other embodiments, the amount of the anti-CD44 monoclonal antibody administered at the first time point may be different from that at the second time point.

While the invention has been described in terms of what is presently considered to be the most practical and preferred Embodiments, it is to be understood that the invention need not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A method for treating a subject suffering from a Flavivirus infection, comprising:
    administering to the subject a pharmaceutical composition comprising a pharmaceutically effective amount of an anti-CD44 antibody and a CD44 small interfering RNA (siRNA), wherein the subject has not developed a warning sign yet and the CD44 siRNA is one selected from the group consisting of SEQ ID NO: 2, SEQ ID NO: 3, SEQ ID NO: 4 and the combination thereof.

2. The method according to claim 1, wherein the Flavivirus infection causes the subject to have an illness being one selected from the group consisting of yellow fever, Japanese encephalitis, dengue fever, West Nile fever, a Zika virus infection and a combination thereof.

3. The method according to claim 1, wherein the subject is a mammal.

4. The method according to claim 1, wherein the subject has a level of a hyaluronan in a serum, and the level is higher than or equal to 70 ng/mL.

5. The method according to claim 1, wherein the warning sign is one selected from the group consisting of an abdominal pain, an abdominal tenderness, a persistent vomiting, a clinical fluid accumulation, a mucosal bleed, a lethargy, a restlessness, a liver enlargement of more than 2 centimeters, an increase in a hematocrit (HCT) concurrent with a rapid decrease in a platelet count, and a combination thereof.

6. The method according to claim 1, wherein the pharmaceutical composition further comprises one selected from the group consisting of a pharmaceutically acceptable carrier, an excipient, a diluent, an adjuvant and a combination thereof.

7. The method according to claim 1, wherein the pharmaceutically effective amount is in a range from 1 mg/kg to 20 mg/kg.

8. The method according to claim 7, wherein the pharmaceutically effective amount is in a range from 4 mg/kg to 8 mg/kg.

9. A method for treating a subject suffering from a Flavivirus infection, comprising:
    administering to the subject a pharmaceutical composition comprising a first pharmaceutically effective amount of an anti-CD44 antibody, wherein the subject has not developed a warning sign yet; and
    subsequently administering to the subject the pharmaceutical composition comprising a second pharmaceutically effective amount of the anti-CD44 antibody,
    wherein the pharmaceutical composition further comprises a CD44 small interfering RNA (siRNA), and the CD44 siRNA is one selected from the group consisting of SEQ ID NO: 2, SEQ ID NO: 3, SEQ ID NO: 4 and the combination thereof.

10. The method according to claim 9, wherein the first pharmaceutically effective amount is equal to the second pharmaceutically effective amount.

11. The method according to claim 9, wherein the second pharmaceutically effective amount of the anti-CD44 antibody is administered at least 24 hours after the first pharmaceutically effective amount of the anti-CD44 antibody was administered.

* * * * *

```
                              SEQUENCE LISTING

<160> NUMBER OF SEQ ID NOS: 4

<210> SEQ ID NO 1
<211> LENGTH: 19
<212> TYPE: RNA
<213> ORGANISM: Artificial Sequence
<220> FEATURE:
<223> OTHER INFORMATION: CD44 siRNA 1

<400> SEQUENCE: 1
gaauauaacc ugccgcuuu                                                        19

<210> SEQ ID NO 2
<211> LENGTH: 19
<212> TYPE: RNA
<213> ORGANISM: Artificial Sequence
<220> FEATURE:
<223> OTHER INFORMATION: CD44 siRNA 2

<400> SEQUENCE: 2
caaguggacu caacggaga                                                        19

<210> SEQ ID NO 3
<211> LENGTH: 19
<212> TYPE: RNA
<213> ORGANISM: Artificial Sequence
<220> FEATURE:
<223> OTHER INFORMATION: CD44 siRNA 3

<400> SEQUENCE: 3
cgaagaaggu gugggcaga                                                        19

<210> SEQ ID NO 4
<211> LENGTH: 19
<212> TYPE: RNA
<213> ORGANISM: Artificial Sequence
<220> FEATURE:
<223> OTHER INFORMATION: CD44 siRNA 4

<400> SEQUENCE: 4
gaucaacagu ggcaaugga                                                        19
```